(12) United States Patent
Grossinger et al.

(10) Patent No.: US 7,523,018 B2
(45) Date of Patent: Apr. 21, 2009

(54) HAIR COLORING SYSTEM

(75) Inventors: Nadav Grossinger, Rechovot (IL); Eli Benny, Rishon-LeZion (IL); Israel Grossinger, Rechovot (IL); Avigdor Scherz, Rechovot (IL); Michel Mercier, Tel-Aviv (IL)

(73) Assignee: SeeThrough Ltd., Nes Ziona (IL)

( * ) Notice: Subject to any disclaimer, the term of this patent is extended or adjusted under 35 U.S.C. 154(b) by 0 days.

(21) Appl. No.: 11/066,205

(22) Filed: Feb. 28, 2005

(65) Prior Publication Data

US 2006/0195300 A1  Aug. 31, 2006

(51) Int. Cl.
*H04B 15/00* (2006.01)
(52) U.S. Cl. .......... 702/189; 702/190; 382/100
(58) Field of Classification Search .......... None
See application file for complete search history.

(56) References Cited

U.S. PATENT DOCUMENTS

| | | | |
|---|---|---|---|
| 4,434,467 A | | 2/1984 | Scott |
| 5,264,001 A * | | 11/1993 | Arifoglu et al. .......... 8/111 |
| 5,609,484 A | | 3/1997 | Hawiuk |
| 5,643,341 A * | | 7/1997 | Hirsch et al. .......... 8/405 |
| 6,067,504 A | | 5/2000 | MacFarlane et al. |
| 6,157,445 A | | 12/2000 | MacFarlane et al. |
| 6,308,088 B1 | | 10/2001 | MacFarlane et al. |
| 6,314,372 B1 | | 11/2001 | MacFarlane et al. |
| 6,330,341 B1 | | 12/2001 | MacFarlane et al. |
| 6,707,929 B2 | | 3/2004 | Marapane et al. |
| 6,810,130 B1 * | | 10/2004 | Aubert et al. .......... 382/100 |
| 2002/0193956 A1 * | | 12/2002 | Van de Capelle et al. ..... 702/81 |
| 2004/0000015 A1 | | 1/2004 | Grossinger et al. |
| 2004/0105830 A1 * | | 6/2004 | Boswell et al. .......... 424/70.2 |
| 2005/0177032 A1 * | | 8/2005 | Grossinger et al. .......... 600/310 |
| 2006/0281994 A1 * | | 12/2006 | Miyamae et al. .......... 600/473 |

FOREIGN PATENT DOCUMENTS

| | | |
|---|---|---|
| EP | 0564 125 | 6/1993 |
| EP | 1138374 | 10/2001 |
| WO | WO 2005/013188 | 2/2005 |

* cited by examiner

*Primary Examiner*—Bryan Bui
*Assistant Examiner*—Jonathan Teixeira Moffat

(57) ABSTRACT

A system for determining hair color treatment, including a processor. The processor is configured for: receiving as input an initial spectrum of a sample of hair, the initial spectrum having a wavelength range; calculating a new spectrum of the hair due to a hypothetical hair color treatment as a direct function of the initial spectrum; and outputting data to a device, the data being based upon the step of calculating. The system also includes a spectrum analyzer configured for producing the initial spectrum and a display device configured for displaying a color and hair color treatment instructions based on the data. An alternate embodiment of the invention includes a color mixing device configured for dispensing a hair color treatment based on the data.

57 Claims, 9 Drawing Sheets

HAIR COLORING SYSTEM

FIELD AND BACKGROUND OF THE INVENTION

The present invention relates to hair coloring and, in particular, it concerns determining a hair color treatment for hair including previously dyed hair.

By way of introduction, different hair samples react differently to the process of bleaching and dyeing due to, amongst other factors, the different chemical pigment structure of the hair as well as the condition of the hair to be treated. The prior art includes many methods which try to predict final hair color in order to minimize error and increase customer satisfaction with the hair color products.

Of relevance to the present invention is U.S. Pat. No. 4,434,467 to Scott. The patent to Scott describes a method whereby the customer chooses a color from a database that is the closest match to his or her own hair color. The customer then chooses a desired final color from the database. The computer then suggests a treatment based on the manufacturer instructions. A shortcoming of the aforementioned system is that the customer has to determine by visual comparison, the closest match to his or her own hair color. A further shortcoming of the aforementioned system is that the system is limited to hair treatments, which are based upon a fixed and limited selection of initial hair colors, thereby not taking into account the individual's hair color.

Also of relevance to the present invention is U.S. Pat. No. 5,609,484 to Hawuik. Hawuik teaches the use of color filament swatches to recreate the initial hair color and then to add color filament swatches, which are related to a known hair dye, to see how the initial hair color is affected by the hair dye. A shortcoming of the aforementioned system is that the system is not accurate. A further shortcoming of the aforementioned system is that determining the initial color involves a high degree of estimation. An additional shortcoming of the aforementioned system is that this system does not address bleaching of the initial hair color.

Of most relevance to the present invention is U.S. Pat. Nos. 6,067,504, 6,157,445, 6,308,088, 6,314,372 and 6,330,341 to MacFarlane, et el. These patents discuss a method, which first includes obtaining a reflectance spectrum from a sample of hair. The coefficients of the Hunter L, a and b color coordinates of the reflectance spectrum of the hair sample are then analyzed by a computer. The initial hair color is then classified by the computer according to a range of coefficients of the color coordinates stored in a lookup table. A user then chooses a desired hair color from a choice of possible final colors. The computer then determines the appropriate hair treatment based upon a hair treatment stored in a lookup table for the initial hair color and the desired final hair color. A shortcoming of the aforementioned system is due to the initial hair color being classified according to an artificial color, which fits into a range of possible colors. Therefore, the suggested hair treatment does not accurately reflect the users initial hair color. A further shortcoming of the aforementioned system is that the creation and maintenance of the hair treatment lookup table requires a vast number of experiments. For example, for each hair dye, experiments are needed for all the possible initial and final hair colors that can be achieved for that dye.

Also of relevance to the present invention is U.S. Pat. No. 6,707,929 to Marapane, et al. Marapane, et al. teaches calculating final color coordinates (such as L, a, b or RGB) of hair by using equations which define the relationship between the untreated hair color coordinates and the treated hair color coordinates for a particular dye. This method overcomes some of the shortcomings of the MacFarlane, et al. patents. Nevertheless, all the above methods (including Marapane, et al.) use a color coordinate system, such as L, a, b, or RGB. Color coordinates can be misleading in certain cases. For example, two samples of hair, which look substantially the same to the human eye may have the same L, a, b color coordinate values even though they have different spectra of reflectance, and therefore, different concentrations of components. For example, one natural blond hair sample which is colored with dye A, may have the same color coordinates as another hair sample, say, a brown hair colored with a dye B. Moreover, a large number of hair samples, each having different reflectance spectra, may all generate the same or very similar color coordinates especially as the cuticles and white envelope of the hair also contribute to the reflectance spectrum. However, the same hair treatment applied to these hair samples will generate different final hair colors due to different initial concentrations of each of their components. Therefore, simply looking at the L, a, b color coordinates or other color coordinates may lead to spurious results.

Moreover, none of the abovementioned methods models the color treatment process based on the chemical properties of hair.

Mixing hair dyes is used widely at hair salons in order to help a customer obtain a desired hair color that a single hair dye cannot give. None of the abovementioned methods predicts the final color of hair that is colored with a mixture of two or more hair dyes without the need to perform experiments on specific combinations of dyes. In other words, all the above mentioned methods require coloring a large quantity of different hair samples with every possible mixture and building a model for each mixture separately. Therefore, it is not feasible with the prior art to cover all possible color mixtures in order to provide a global solution to this problem.

Also, the prior art methods do not effectively address coloring previously dyed hair.

There is therefore a need for a hair color determination system and method for accurately determining a suitable hair color treatment for all types of hair including natural hair as well as previously dyed and/or bleached hair and including using a mixture of two or more dyes.

SUMMARY OF THE INVENTION

The present invention is a hair color determination system and method of operation thereof.

According to the teachings of the present invention there is provided, a system for determining hair color treatment, comprising: a processor configured for: (i) receiving as input an initial spectrum of a sample of hair, the initial spectrum having a wavelength range; (ii) calculating a new spectrum of the hair due to a hypothetical hair color treatment as a direct function of the initial spectrum; and (iii) outputting data to a device, the data being based upon the step of calculating.

According to a further feature of the present invention, there is also provided a spectrum analyzer configured for producing the initial spectrum.

According to a further feature of the present invention, there is also provided a display device configured for displaying a color based on the data.

According to a further feature of the present invention, there is also provided a display device configured for displaying hair color treatment instructions based on the data.

According to a further feature of the present invention, there is also provided a color mixing device configured for dispensing a hair color treatment based on the data.

According to a further feature of the present invention, the processor is further configured for determining a treatment for the hair that gives the hair a desired spectrum.

According to a further feature of the present invention, the direct function is substantially non-additive.

According to a further feature of the present invention, the calculating is performed by calculating the new spectrum based on multiplying the initial spectrum by a spectral change function over the wavelength range, a value of the spectral change function varying over the wavelength range.

According to a further feature of the present invention, the spectral change function includes a spectral change component due to a bleaching effect of the hypothetical hair color treatment.

According to a further feature of the present invention, the spectral change component is dependent upon a reflectance of the hair.

According to a further feature of the present invention, the spectral change function also includes a spectral change component due to a dyeing effect of the hypothetical hair color treatment.

According to a further feature of the present invention, the calculating includes: (i) for each of a plurality of discrete wavelengths within the wavelength range, calculating a new optical value for the hair for one of the discrete wavelengths as a function of an initial optical value of the hair at the one discrete wavelength, thereby giving a set of new optical values for the hair; and (ii) forming the new spectrum from the set of new optical values.

According to a further feature of the present invention, the function of the initial optical value varies over the wavelength range.

According to the teachings of the present invention there is also provided, a system for determining hair color treatment, comprising a processor configured for: (i) receiving as input an initial spectrum of a sample of hair, the initial spectrum having a wavelength range; (ii) determining a hair color treatment for the hair as a direct function of the initial spectrum and a desired spectrum of the hair; and (iii) outputting data to a device, the data being based upon the step of determining.

According to a further feature of the present invention, there is also provided a spectrum analyzer configured for producing the initial spectrum.

According to a further feature of the present invention, there is also provided a display device configured for displaying hair color treatment instructions based on the data.

According to a further feature of the present invention, there is also provided a color mixing device configured for dispensing a hair color treatment based on the data.

According to a further feature of the present invention, the function is substantially non-additive.

According to a further feature of the present invention, the determining includes: calculating a spectral change function by dividing the desired spectrum by the initial spectrum over the wavelength range; and determining the treatment from the spectral change function.

According to a further feature of the present invention, the spectral change function includes a spectral change component due to a bleaching effect of the hypothetical hair color treatment.

According to a further feature of the present invention, the spectral change component is dependent upon a reflectance of the hair.

According to a further feature of the present invention, the spectral change function also includes a spectral change component due to a dyeing effect of the hypothetical hair color treatment.

According to a further feature of the present invention, the determining includes for each of a plurality of discrete wavelengths within the wavelength range, calculating a new optical value for the hair for one of the discrete wavelengths as a function of an initial optical value of the hair at the one discrete wavelength, thereby giving a set of new optical values for the hair.

According to a further feature of the present invention, the function of the initial optical value varies over the wavelength range.

According to the teachings of the present invention there is also provided, a system for determining treatment of hair using a first relative concentration of a first hair color treatment and a second relative concentration of a second hair color treatment, the first hair color treatment having an associated first spectral change function for use in determining a first new spectrum of the hair after application of only the first hair color treatment, the second hair color treatment having an associated second spectral change function for use in determining a second new spectrum of the hair after application of only the second hair color treatment, the system comprising a processor configured for: (i) receiving as input an initial spectrum of the hair, the initial spectrum having a wavelength range; (ii) calculating a new spectrum of the hair due to a hypothetical hair color treatment of applying the first relative concentration of the first hair color treatment and the second relative concentration of a the second hair color treatment to the hair, the calculating being based upon at least one of: (I) apportioning the first spectral change function and the second spectral change function by the first relative concentration and the second relative concentration, respectively; and (II) apportioning the first new spectrum and the second new spectrum by the first relative concentration and the second relative concentration, respectively; and (iii) outputting data to a device, the data being based on the step of calculating.

According to a further feature of the present invention, the calculating is based on at least one of: (i) raising the first spectral change function to a power of the first relative concentration and raising the second spectral change function to a power of the second relative concentration; and (ii) raising the first new spectrum to a power of the first relative concentration and raising the second new spectrum to a power of the second relative concentration.

According to a further feature of the present invention, there is also provided a spectrum analyzer configured for producing the initial spectrum.

According to a further feature of the present invention, there is also provided a display device configured for displaying a color based on the data.

According to a further feature of the present invention, there is also provided a display device configured for displaying hair color treatment instructions based on the data.

According to a further feature of the present invention, there is also provided a color mixing device configured for dispensing a hair color treatment based on the data.

According to the teachings of the present invention there is also provided, a method for determining hair color treatment, comprising the steps of: (i) receiving as input an initial spectrum of a sample of hair, the initial spectrum having a wavelength range; and (ii) calculating a new spectrum of the hair due to a hypothetical hair color treatment as a direct function of the initial spectrum.

According to a further feature of the present invention, there is also provided the step of displaying a color based on the new spectrum.

According to a further feature of the present invention, there is also provided the step of displaying hair color treatment instructions based on the new spectrum.

According to a further feature of the present invention, there is also provided the step of dispensing a hair color treatment based on the new spectrum.

According to a further feature of the present invention, there is also provided the step of determining a treatment for the hair that gives the hair a desired spectrum.

According to a further feature of the present invention, the direct function is substantially non-additive.

According to a further feature of the present invention, the calculating is performed by calculating the new spectrum based on multiplying the initial spectrum by a spectral change function over the wavelength range, a value of the spectral change function varying over the wavelength range.

According to a further feature of the present invention, the spectral change function includes a spectral change component due to a bleaching effect of the hypothetical hair color treatment.

According to a further feature of the present invention, the spectral change component is dependent upon a reflectance of the hair.

According to a further feature of the present invention, the spectral change function also includes a spectral change component due to a dyeing effect of the hypothetical hair color treatment.

According to a further feature of the present invention, the calculating includes: (i) for each of a plurality of discrete wavelengths within the wavelength range, calculating a new optical value for the hair for one of the discrete wavelengths as a function of an initial optical value of the hair at the one discrete wavelength, thereby giving a set of new optical values for the hair; and (ii) forming the new spectrum from the set of new optical values.

According to a further feature of the present invention, the function of the initial optical value varies over the wavelength range.

According to a further feature of the present invention, a computer software product, comprising a computer readable medium in which computer instructions are stored, which instructions when read by a computer, causes the computer to determine the hair color treatment, the instructions including the above method steps.

According to the teachings of the present invention there is also provided, a method for determining hair color treatment, comprising the steps of: (i) receiving as input an initial spectrum of a sample of hair, the initial spectrum having a wavelength range; and (ii) determining a hair color treatment for the hair as a direct function of the initial spectrum and a desired spectrum of the hair.

According to a further feature of the present invention, there is also provided the step of displaying hair color treatment instructions based on the determining.

According to a further feature of the present invention, there is also provided the step of dispensing a hair color treatment based on the determining.

According to a further feature of the present invention, the function is substantially non-additive.

According to a further feature of the present invention, the determining includes: calculating a spectral change function by dividing the desired spectrum by the initial spectrum over the wavelength range; and determining the treatment from the spectral change function.

According to a further feature of the present invention, the spectral change function includes a spectral change component due to a bleaching effect of the hypothetical hair color treatment.

According to a further feature of the present invention, the spectral change component is dependent upon a reflectance of the hair.

According to a further feature of the present invention, the spectral change function also includes a spectral change component due to a dyeing effect of the hypothetical hair color treatment.

According to a further feature of the present invention, the determining includes for each of a plurality of discrete wavelengths within the wavelength range, calculating a new optical value for the hair for one of the discrete wavelengths as a function of an initial optical value of the hair at the one discrete wavelength, thereby giving a set of new optical values for the hair.

According to a further feature of the present invention, the function of the initial optical value varies over the wavelength range.

According to a further feature of the present invention, a computer software product, comprising a computer readable medium in which computer instructions are stored, which instructions when read by a computer, causes the computer to determine the hair color treatment, the instructions including the above method steps.

According to the teachings of the present invention there is also provided, a method for determining a hair color treatment using a first relative concentration of a first hair color treatment and a second relative concentration of a second hair color treatment, the first hair color treatment having an associated first spectral change function for use in determining a first new spectrum of the hair after application of only the first hair color treatment, the second hair color treatment having an associated second spectral change function for use in determining a second new spectrum of the hair after application of only the second hair color treatment, the method including the steps of: (i) receiving as input an initial spectrum of the hair, the initial spectrum having a wavelength range; and (ii) calculating a new spectrum of the hair due to a hypothetical hair color treatment of applying the first relative concentration of the first hair color treatment and the second relative concentration of a the second hair color treatment to the hair, the calculating being based upon at least one of: (I) apportioning the first spectral change function and the second spectral change function by the first relative concentration and the second relative concentration, respectively; and (II) apportioning the first new spectrum and the second new spectrum by the first relative concentration and the second relative concentration, respectively.

According to a further feature of the present invention, the calculating is based on at least one of: (i) raising the first spectral change function to a power of the first relative concentration and raising the second spectral change function to a power of the second relative concentration; and (ii) raising the first new spectrum to a power of the first relative concentration and raising the second new spectrum to a power of the second relative concentration.

According to a farther feature of the present invention, a computer software product, comprising a computer readable medium in which computer instructions are stored, which instructions when read by a computer, causes the computer to determine the hair color treatment, the instructions including the above method steps.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
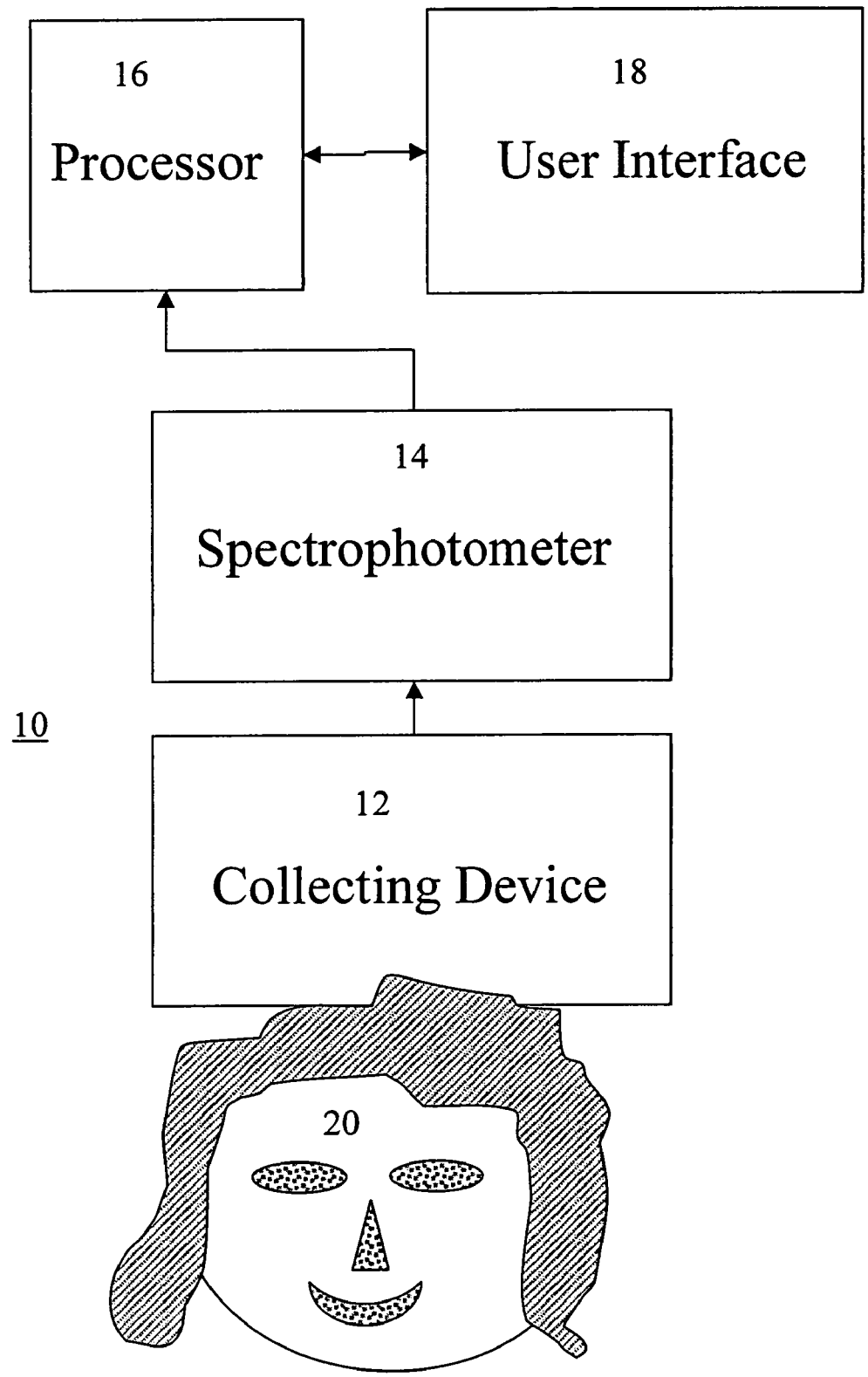
FIG. 1 is a schematic view of a hair color determination system that is constructed and operable in accordance with a preferred embodiment of the invention.

The present invention is a hair color determination system and method of operation thereof.

The principles and operation of a hair color determination system according to the present invention may be better understood with reference to the drawings and the accompanying description.

By way of introduction, the present invention teaches predicting final hair color resulting from a process of treating natural hair, previously dyed and/or bleached hair with a hair color treatment. The term "hair color treatment" is defined herein to include dyeing and/or bleaching hair with a single product or a mixture of two or more products. Generally, hair color treatments to dye hair also include a bleaching agent which opens up the cuticle and allows the dye to enter the hair. Therefore, even a hair color product meant for only dyeing the hair also includes a certain amount of bleaching substance which has a bleaching effect on the hair. The term "dye" or "dyeing" is defined herein as adding color pigments to the hair. The term "bleach" or "bleaching" is defined herein as replacing pigments with an oxidized form. The present invention is based on isolating the dye and bleaching spectral change components caused by the hair color treatment and calculating a final or new reflectance spectrum as a direct function of an initial reflectance spectrum. The term "final" or "new" reflectance spectrum is defined as the calculated reflectance spectrum of hair after taking into account a proposed or hypothetical hair color treatment. The term "initial" reflectance spectrum is defined as a measured reflectance spectrum of a hair sample prior to this hair color treatment. Nevertheless, it should be noted that the hair sample may be previously dyed and/or bleached prior to this current proposed hair color treatment. The term "direct function" is defined herein as a function that transforms the initial spectrum into a final (or new or spectral change function) without converting the input spectrum into a non-spectral color representation such as the (L, a, b) representation used by Marapane et al. and by MacFarlane et al. or the coefficients of natural hair factors taught by the Applicant in published US patent application no. 2004/0000015 to Grossinger, et al., which is incorporated by reference for all purposes as if fully set forth herein. The initial reflectance spectrum includes natural hair factors (Eumelanin and Pheomelanin) as well as factors relating to previous dyes (if applicable). US patent application no. 2004/0000015 to Grossinger, et al. requires that the factors of the hair be known in advance. With previously dyed hair, the dye factor is generally not known, therefore a final reflectance spectrum cannot be determined using patent application no. 2004/0000015 to Grossinger, et al. However, with the present invention, the factors making up the hair do not need to be known in order to calculate the final reflectance spectrum. Therefore, the present invention can also be used for calculating a final reflectance spectrum of previously dyed hair.

The present invention teaches two approaches to apply the abovementioned teaching. The first approach involves defining a spectral change function having a dyeing and a bleaching component, which affects all wavelengths of the initial reflectance spectrum in order to arrive at a final reflectance spectrum. The second approach involves defining a spectral change function for each wavelength separately and then applying each spectral change function to each wavelength of the initial reflectance measurement in order to arrive at a final reflectance spectrum.

Each of these approaches is described in more detail below. The first approach is described with reference to FIGS. 2 to 7. The second approach is described with reference to FIGS. 8 to 10. A preferred method for application of these abovementioned approaches is described with reference to FIG. 11.

Reference is now made to FIG. 1, which is a schematic view of a hair color determination system 10 that is constructed and operable in accordance with a preferred embodiment of the invention. System 10 includes a light collecting device 12, a spectrophotometer 14, a processor 16 and a user interface 18. Light collecting device 12 is typically an integrating sphere or other suitable light-integrating device. Light collecting device 12 has a sampling port (not shown) which is placed on the hair of a customer 20. Spectrophotometer 14 analyzes the light collected by light collecting device 12 in order to produce a reflectance spectrum of the hair of customer 20. The reflectance spectrum typically has a wavelength range between 380 and 750 nanometers. It should be noted that the reflectance spectrum is a measure of reflectance over the wavelength range. The measure of reflectance is a relative quantity and is typically represented as a percentage of a white reflective reference material. Each spectrophotometer is sold with a reference material having a known reflectance spectrum in order to calibrate the spectrophotometer before use. Once a spectrophotometer is calibrated with its own calibration material, the spectrophotometer should give the same reflectance spectrum in percentage terms of the same sample as any other calibrated spectrophotometer. Processor 16 receives the reflectance spectrum as an input for performing calculations in order to determine an appropriate hair color treatment for customer 20. The steps performed by processor 16 are described in more detail with reference to FIGS. 2 to 11. User interface 18 typically includes a mouse, keyboard and a display device for customer 20 to choose a desired hair color as well as to give instructions to the hairdresser of which hair color treatments to apply.

Figure 2:
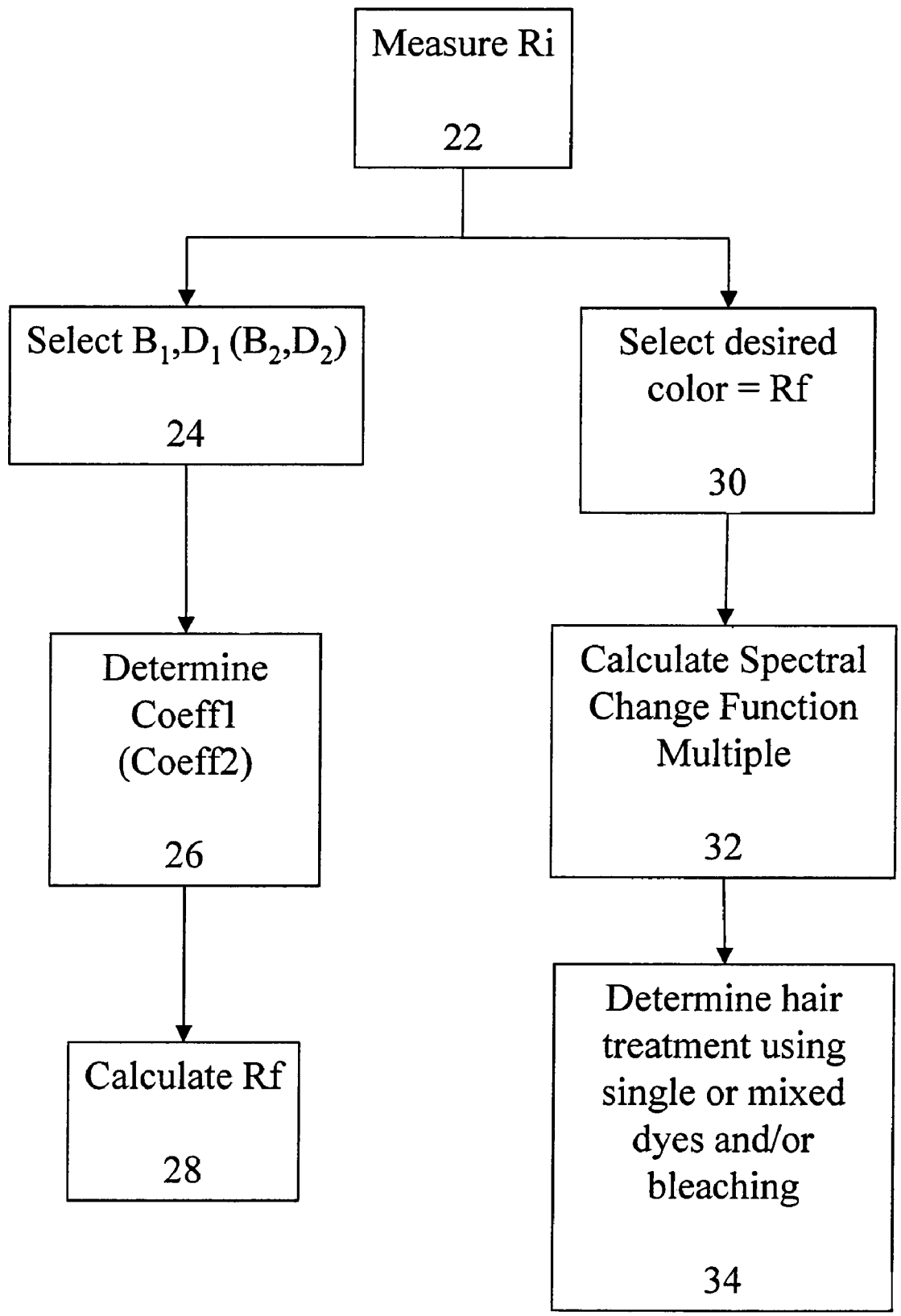
FIG. 2 is a flow chart showing a first approach to calculating a new reflectance spectrum for use with the system of FIG. 1.

Reference is now made to FIG. 2, which is a flow chart showing a first approach to calculating a new reflectance spectrum for use with system 10 of FIG. 1. By way of introduction, given an initial reflectance spectrum of a hair sample, the modeling of the coloring process is defined by means of multiplying the spectral changes caused by both the dye pigments and bleaching effect of the hair color treatment tube. In other words, a new reflectance spectrum is calculated by multiplying an initial reflectance spectrum by a dye and bleaching spectral change function. The value of the spectral change functions varies with wavelength. It is assumed that the quantity of dye pigments added in the coloring process remains constant in every hair sample and so the dye spectral change function is independent of the initial reflectance of the hair. It is assumed that the bleaching spectral change function varies from one hair sample to another due to the concentration and ratios of the hair's pigments prior to treatment. Therefore, the bleaching spectral change function is dependent on the initial reflectance of the hair, as will be discussed in more detail below with reference to FIGS. 4 and 5. Unlike prior art methods of predicting color results based on the absorption of the additional dye added, the method of the present invention also considers the chemical spectral change of the initial hair pigments due to the bleach ingredient of the hair color treatment tube.

The final hair reflectance spectrum (after coloring) is defined by the following equation:

$$R_f = R_i \cdot D \cdot B^{Exp} \quad \text{(Equation 1.1),}$$

where $R_f$ is the reflectance spectrum after coloring (final reflectance), $R_i$ is the reflectance spectrum before coloring (initial reflectance), D is the spectral change function caused by the dye pigments, $B^{Exp}$ is the spectral change function caused by the bleaching effect. The values of both B and D are wavelength dependent. Exp is the exponent of B. B and D are the same for any one hair color treatment. B and D are independent of the hair sample. Exp on the other hand is dependent on the total initial reflectance of the hair sample. For convenience, $B^{exp}$ is termed as the "specific bleaching spectral change function" as it depends on a specific total initial reflectance of hair, and B is termed as the "general bleaching spectral change function" as B is independent of the hair sample. The determination of B, D and Exp is described below in more detail with reference to FIGS. 3 to 5. The general bleaching spectral change function, B and the dye spectral change function, D, are determined for each hair color treatment tube using several hair samples as will be described below in more detail with reference to FIG. 3.

Once models are characterized for any two or more hair color treatments separately, the final reflectance spectrum due to coloring with a mixture of hair treatments is expressed as follows:

$$R_f = R_i \cdot (D_1 \cdot B_1^{Exp1})^a \cdot (D_2 \cdot B_2^{Exp2})^b \quad \text{Equation 1.2,}$$

where $D_1$ and $D_2$ are the dye spectral change functions for hair color treatment 1 and hair color treatment 2, respectively, $B_1$ and $B_2$ are the general bleach spectral change functions for hair color treatment 1 and hair color treatment 2, respectively, $Exp_1$ and $Exp_2$ are the bleaching exponents for hair color treatment 1 and hair color treatment 2 respectively, a is the relative concentration of hair color treatment 1 in the mixture and b is the relative concentration of hair color treatment 2 in the mixture. Therefore, a+b=1, by definition. It will be appreciated by those ordinarily skilled in the art that if more than two hair color treatments are used then equation 1.2 includes another multiplicative factor for each hair color treatment.

Therefore, equation 1.2 is used to determined a new reflectance spectrum from an initial reflectance spectrum due to a combination of hair color treatments. Unlike the prior art, it is not necessary to perform experiments for each and every possible hair color treatment mixture. The method of the present invention allows calculation of a new reflectance spectrum based upon the same spectral change functions of the hair color treatments when the hair color treatments are used by themselves without mixing. In other words, each hair color treatment has associated spectral change functions (dye and bleach) for use in determining a new spectrum of the hair after application of only that hair color treatment by itself. Nevertheless, the same spectral change functions are also used in equation 1.2 by apportioning the spectral change functions by the relative concentration of the hair color treatment in the mixture as a whole.

Additionally, as a+b=1, rearranging equation 1.2 gives, $$R_f = R_i^a \cdot R_i^b \cdot (D_1 \cdot B_1^{Exp1})^a \cdot (D_2 \cdot D_2^{Exp2})^b \quad \text{Equation 1.3.}$$

Therefore, $$R_f = (R_i \cdot D_1 \cdot B_1^{Exp1})^a \cdot (R_i \cdot D_2 \cdot B_2^{Exp2})^b \quad \text{Equation 1.4.}$$

Therefore, it is seen that, $$R_f = (R_{f1})^a \cdot (R_{f2})^b \quad \text{Equation 1.5,}$$

where $R_{f1}$ and $R_{f2}$ are the final reflectance spectra calculated for hair color treatment 1 and hair color treatment 2, respectively, using equation 1.1. Therefore, equation 1.5 is used to determined a new reflectance spectrum from two final reflectance spectra due to a combination of hair color treatments. Unlike the prior art, it is not necessary to perform experiments for each and every possible hair color treatment mixture. The method of the present invention allows calculation of a new reflectance spectrum based upon apportionment of the final reflectance spectra using equation 1.5. The final reflectance spectra are calculated for hair color treatments used by themselves without mixing using equation 1.1 for each hair color treatment.

Therefore, a new spectrum of hair is calculated using equation 1.2 by apportioning the spectral change functions of the one hair color treatment and the spectral change functions of another hair color treatment, by the relative concentrations of the hair color treatments in the mixture, respectively. Alternatively, a new spectrum of hair is calculated using equation 1.5 by apportioning the final reflectance spectrum due to only using one hair color treatment and the final reflectance spectrum due to only using another hair color treatment, by the relative concentrations of the hair color treatments in the mixture, respectively. It is seen from equations 1.2 and 1.5 that apportionment is performed by raising the factors in the equation to the power of the relative concentrations. However, it will be appreciated by those ordinarily skilled in the art that the factors could be apportioned by multiplying the factors by a suitable fraction.

Equations 1.1, 1.2 and 1.5 are typically used to calculate a new reflectance spectrum as a direct function of an initial reflectance spectrum and a hypothetical hair treatment. However, it will be appreciated by those ordinarily skilled in the art that equations 1.1, 1.2 and 1.5 can be used to determine a hypothetical hair treatment as a direct function of an initial reflectance spectrum and a desired final reflectance spectrum. Both these methods are described below.

The first method is for calculating a new reflectance spectrum due to a hypothetical hair treatment as a direct function of an initial reflectance spectrum. First, an initial reflectance spectrum is measured by spectrophotometer 14 (block 22). Second, processor 16 receives the initial reflectance spectrum, having a wavelength range, as an input. Third, at least one hypothetical hair treatment is selected having associated D and B (block 24). Fourth, Exp is determined for each hair color treatment a new (block 26). Finally, a new spectrum of the hair due to the hypothetical hair color treatment(s) is calculated using one or more of equations 1.1, 1.2 or 1.5 (block 28). It is seen that the new spectrum is a substantially non-additive function of the hair treatment and the initial reflectance spectrum. The term "substantially non-additive function" is defined herein as a function that includes mathematical operations other than addition and subtraction, even though addition and subtraction form part of the function. For example, the new spectrum is not solely determined by adding the initial spectrum to a spectrum of the dye.

The second method is for calculating a hair treatment as a direct function of an initial reflectance spectrum and a desired reflectance spectrum. First, an initial reflectance spectrum is measured by spectrophotometer 14 (block 22). Second, processor 16 receives the initial reflectance spectrum, having a wavelength range, as an input. Third, a desired reflectance spectrum is selected (block 30). Fourth, using equation 1.1, $R_f$ is divided by $R_i$, over the wavelength range, to give a desired spectral change function multiple of $DB^{Exp}$ (block 32). Finally, for each available hair color treatments and mixtures thereof, $DB^{Exp}$ is calculated in an iterative manner (or for a mixture of hair color treatments $D_1B_1^{Exp1} \cdot D_2B_1^{Exp2}$ is calculated) to see which hair color treatment or mixture thereof provides the closest match to the desired spectral change function multiple of $DB^{Exp}$ (Block 34) in order to determine a suitable hair color treatment. It is seen that the determined hair treatment is a substantially non-additive function of the initial reflectance spectrum and the desired reflectance spectrum.

Equation 1.1 is based on application of Beer's law.

The intensity change of light interacting with a light absorbing material is described by Beer's law as:

$$I_{output} = I_{input} \cdot e^{-\alpha \cdot Exp \cdot l} \qquad \text{Equation 2.1.}$$

where $I_{output}$ is the output intensity of the light, $I_{input}$ is the input intensity of the light, $\alpha$ is the light absorbing characteristic of the material and Exp represents the concentration of the material, l is the propagation length of light in the sample. l is approximated as a constant for all hair samples and therefore is not referenced hereinbelow. Any additional light absorbing substances added to the material is added in a multiplicative manner.

In our case, the output intensity measured, $I_{output}$ is the reflectance spectrum, R. Therefore, the input intensity of the light after reacting with the natural hair pigments and dye remains from previous hair colors gives the initial reflectance spectrum of the hair and therefore, $$R_i = I_{input} \cdot e^{-\alpha_{naturalPigments}} \cdot e^{-\alpha_{previousColors}} \qquad \text{Equation 2.2.}$$

Therefore, after applying a new hair color treatment, the final reflectance spectrum is given by, $$R_f = I_{input} \cdot e^{-\alpha_{naturalPigments}} \cdot e^{-\alpha_{previousColors}} \cdot e^{-\alpha_{newColor}} \qquad \text{Equation 2.3.}$$

For further simplicity, D is defined as the relative transmission of the new dye added, therefore, $$D = e^{-\alpha_{newColor}} \qquad \text{Equation 2.4.}$$

Therefore, substitution of the terms of equation 2.3 with $R_i$ of equation 2.2 and D of equation 2.4 into equation 2.2 gives, $$R_f = R_i \cdot D \qquad \text{Equation 2.5.}$$

It should be noted that the exponents for the light absorption of the natural pigments and previous dyes in the hair have been omitted from equation 2.2 and 2.3. Nevertheless, the light absorbing characteristics of the exponents are included in equation 2.5 as the measured initial reflectance spectrum includes the light absorbing characteristics due to these exponents. The new color exponent is omitted from the equations, as it is assumed that the light absorption of a dye is constant over different hair samples.

Bleaching does not add any light absorbing material to hair. However, bleaching causes a change in the light absorption of the natural hair pigments. This light absorption change applied to the hair pigments that are affected by the bleaching process is represented as a change caused by replacing the pigments from the initial phase (before the bleaching) with oxidized pigments having a relatively higher transmission at all wavelengths thereby causing reflectivity to rise. Therefore, the equation for predicting hair coloring is given by, $$R_f = R_i \cdot C \cdot B^{Exp} \qquad \text{Equation 2.6,}$$

where, $$B^{Exp} = (e^{-\alpha_{AfterBleaching}} / e^{-\alpha_{BeforeBleaching}})^{Exp} \qquad \text{Equation 2.7,}$$

where $B^{Exp}$ is the specific spectral change function caused by bleaching, $\alpha_{BeforeBleaching}$ is the light absorbing characteristics of the pigments affected by bleaching before the oxidation caused by the bleaching material, $\alpha_{AfterBleaching}$ is the absorbing characteristics of the same pigments after bleaching and Exp is the bleaching exponent. Exp is dependent on the natural hair pigment concentrations which are exposed to the bleaching chemical reaction (mainly Eumelanin). Therefore, The value of Exp varies from one hair sample to another. The value of Exp correlates with the total reflectance of hair at certain wavelengths as will be described in more detail with reference to FIGS. 4 and 5.

Figure 3:
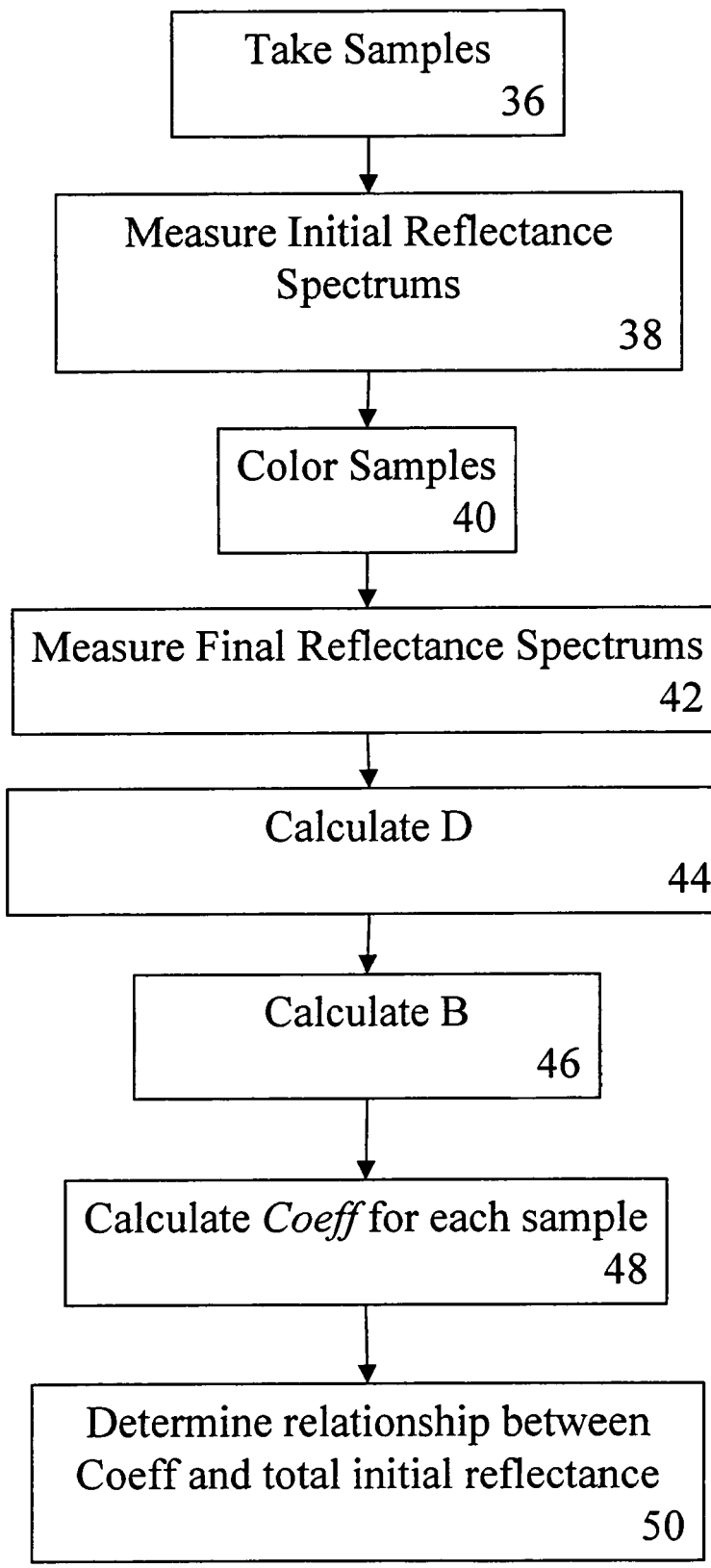
FIG. 3 is a flow chart showing how to create a model for use with the first approach of FIG. 2.

FIG. 3 is a flow chart showing how to create a model for use with the first approach of FIG. 2. The dye and bleach spectral change functions need to be isolated for each hair color treatment (tube) separately. First, several hair samples are taken (block 36). Then, the hair samples have their initial reflectance spectra ($R_i$) measured (block 38). Then, the hair samples are colored using the same hair color treatment (tube) (block 40). After the samples have been colored, the reflectance spectrum ($R_f$) of each of the samples is measured again (block 42). Then, the spectral change function multiple for each hair, $D \cdot B^{Exp}$, is determined for each hair sample by dividing $R_f$ by Ri. The sample of initial hairs (before the coloring) includes at least one hair sample that was previously exposed to a relatively long bleaching treatment (about 30 to 40 minutes). For this previously highly bleached hair sample, the natural pigments that participate in the bleaching chemical reaction during the coloring treatment are exhausted prior to the coloring treatment. Therefore, the bleaching exponent approaches zero. Therefore, the spectral change of the hair caused by the coloring process is mainly due to the dye pigments. Therefore, for this previously highly bleached hair sample, $$\frac{R_f}{R_i} = D \cdot B^{Exp} \xrightarrow{Exp \to 0} D. \qquad \text{Equation 2.8}$$

Therefore, the dye spectral change function, D, is extracted by dividing the final reflectance spectrum by the initial reflectance spectrum for the previously highly bleached hair sample (block 44).

Dividing the average of the spectral change function multiples, $D \cdot B^{Exp}$, for all hairs in the sample, by the dye spectral change function calculated above in block 44, gives an average bleaching spectral change function (block 46). This average bleaching spectral change function is equal to B powered to some exponent. Nevertheless, as Exp is determined in relation to this average bleaching spectral change function (see below), the average bleaching spectral change function calculated here is used for B in equations 1.1 and 1.2.

As described above, the bleaching exponent, Exp is correlated with the initial total reflectance of the hair. The reason for this is that in natural hair (not previously colored), the total reflectance is determined mainly by the dark pigment (Eumelanin) concentration. Those pigments are the main substrate for the bleaching chemical reaction and therefore those pigments affect the bleaching exponent. The method for finding the correlation curve is as follows. First, the total reflectance for each of the initial hair samples is calculated from the initial reflectance spectrum of each sample. Then, for each hair sample, the best bleaching exponent is computed iteratively using equation 1.1 (block 48). The initial and final reflectance spectra have been measured in the steps of blocks 38 and 42, respectively. D was determined in the step of block 44. B was determined in the step of block 46.

Figure 4:
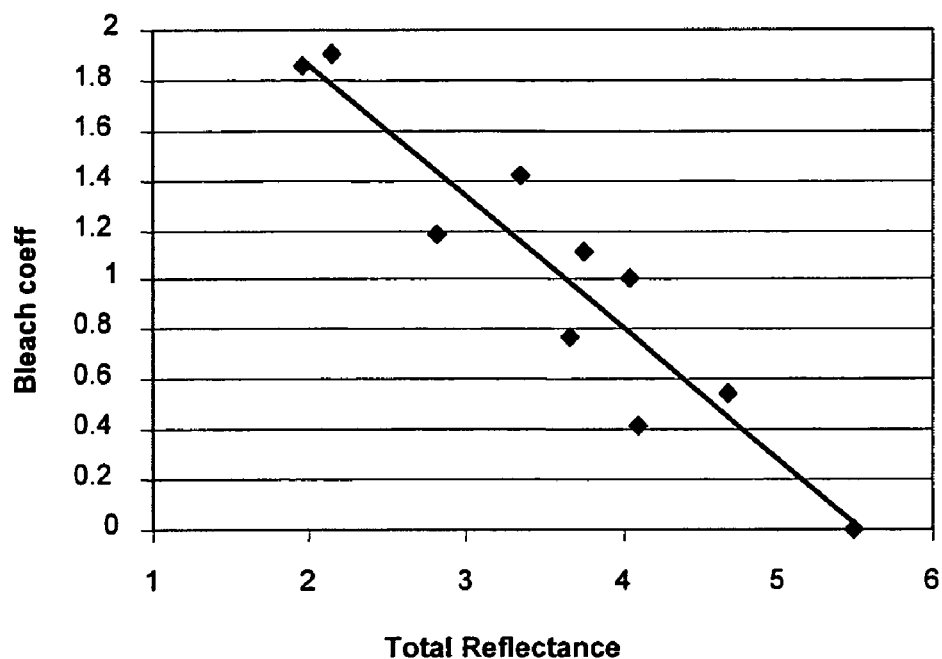
FIG. 4 is a graph of total reflectance against a value of the bleaching exponent for natural hair samples for use with the first approach of FIG. 2.

Reference is now also made to FIG. 4, which is a graph of total reflectance against a value of the bleaching exponent for natural hair samples for use with the first approach of FIG. 2. The next step is to match the initial total reflectances determined above to the bleaching exponents computed in the step of block 48 in order to find a function that represents the exponent as a function of the initial total reflectance (block 50). It is seen from FIG. 4 that the bleaching exponent varies substantially linearly with total initial reflectance.

Figure 5:
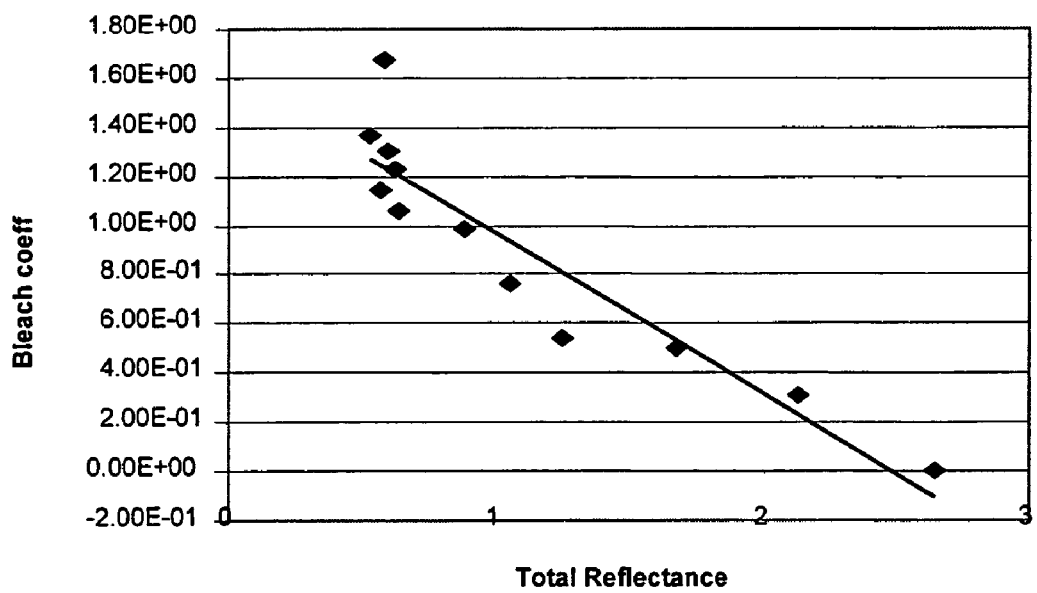
FIG. 5 is a graph of total reflectance against a value of the bleaching exponent for previously dyed hair samples for use with the first approach of FIG. 2.

Reference is now made to FIG. 5, which is a graph of total reflectance against a value of the bleaching exponent for previously dyed hair samples for use with the first approach of FIG. 2. Previously dyed hair samples react the same way as natural hair samples, except that the previous dye affects the hair reflectivity which causes a disorder in the correlation between the bleaching exponent and the initial total reflectance. However, it is found that most artificial colors mainly affect the red side of the hair spectrum which is the most reflective. Therefore, by avoiding this range so as to determine the relationship between the bleaching exponent and the initial total reflectance using data in the 380 to 625 nanometers wavelength range, achieves a good correlation amongst the data. It should be noted that calculating the initial total reflectance using 380 to 625 nanometers range is only needed for predicting the correct bleaching exponent for a specific hair sample. Once the bleaching exponent is determined, the prediction of the final reflectance spectrum is performed for the full range of 380 to 750 nanometers.

It should also be noted that the bleaching effect for previously dyed hair is smaller and less effective than the bleaching effect for natural hair. As a result the bleaching exponent for previously dyed hair is smaller compared to natural hair. Therefore an inaccuracy in the prediction of the bleaching exponent for previously dyed hair does not significantly affect the calculated final reflectance spectrum.

Therefore, using the step of block 50, the bleaching exponent, Exp is determined for any hair sample for a particular hair color treatment.

Figure 6:
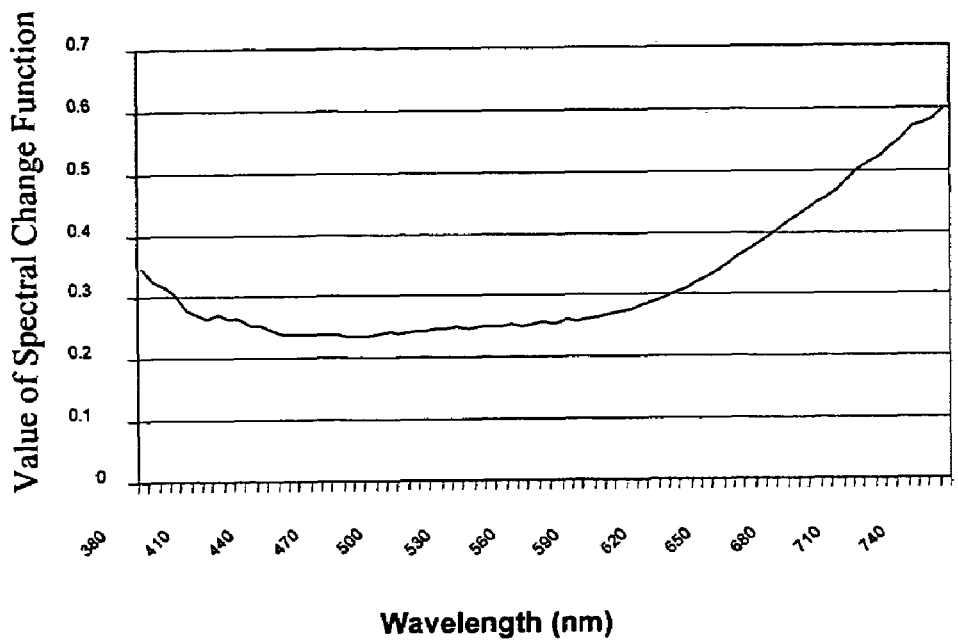
FIG. 6 is a sample dye spectral change component for use with the first approach of FIG. 2.
Figure 7:
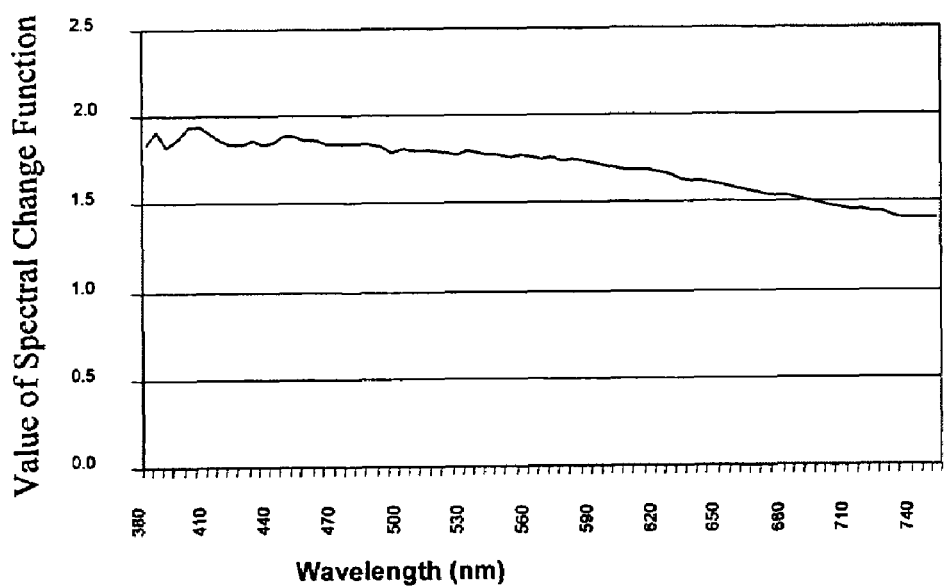
FIG. 7 is a sample bleaching spectral change component for use with the first approach of FIG. 2.

Reference is now made to FIG. 6, which is a sample dye spectral change function for use with the first approach of FIG. 2. Reference is now made to FIG. 7, which is a sample bleaching spectral change component for use with the first approach of FIG. 2. It is seen from FIGS. 6 and 7 that the dye and bleaching spectral change functions vary non-linearly with wavelength.

The method described above is also used, with modifications, in order to determine the effect of only bleaching hair without using a dye. In particular equation 1.1 does not include the dye spectral change function, and therefore, $$R_f = R_i \cdot B^{Exp} \qquad \text{Equation 2.9.}$$

By way of introduction, a dye is normally applied in accordance with the manufacturer's instructions and is applied for a particular length of time. However, for bleaching, the application time varies greatly and depends on how much bleaching is to be performed. Therefore, since time is a variant in this kind of treatment, accurate prediction of the final color of bleached hair helps determine the required duration of the bleaching process. Another variable in the bleaching process is the oxygen concentration used (3%, 6%, 9% or 12%) in order to reach the desired target color. Therefore, in order to isolate the spectral change caused by the bleaching process, several hair samples are taken. The initial reflectance spectra, $R_i$, of the hair samples are measured. The samples are then bleached. The bleaching is performed for a specific time and oxygen concentration. The reflectance spectra, $R_f$ of the samples are then measured again after bleaching. The isolation of the general bleaching spectral change function, B, is performed by dividing the reflectance spectrum after the bleaching by the reflectance spectrum before the bleaching, for each sample. This step is similar to the step of block 46. All the calculated B functions are then averaged to arrive at a better result. Similarly, the bleaching exponent is correlated with the total initial reflectance of the hair. Therefore, the step of block 50 is performed to determine the relationship between the bleaching exponent and the total initial reflectance of hair. Once this step is performed, the bleaching exponent for any hair sample can be calculated.

As state above, the duration of the bleaching affects the final bleaching result. Therefore, the bleaching exponent is also dependent on the duration of the bleaching. The longer the bleaching process is, the greater the value of the bleaching exponent is. Therefore, experiments are performed using several hair samples of different initial colors. Each sample is bleached for a short period (2 to 4 minutes) and then a reflectance spectrum is measured. The same samples are then bleached for an additional short period of time. The reflectance spectra are again measured. This process is repeated 7 to 10 times for the same hair samples. The data obtained is then used to determine the relationship between the bleaching exponent, Exp, and the total initial reflectance of the hair and the bleaching time using linear regression or iterative methods. Therefore, equation 2.9 is used to determine a final reflectance spectrum of hair due to bleaching by a particular concentration of bleaching solution for a certain time period. It should be noted that B is independent of the bleaching time and the initial total reflectance. B is valid only for a particular concentration of bleaching solution. If another concentration of bleaching solution is being used, the above experiments and calculations need to be repeated for the new concentration of bleaching solution.

Figure 8:
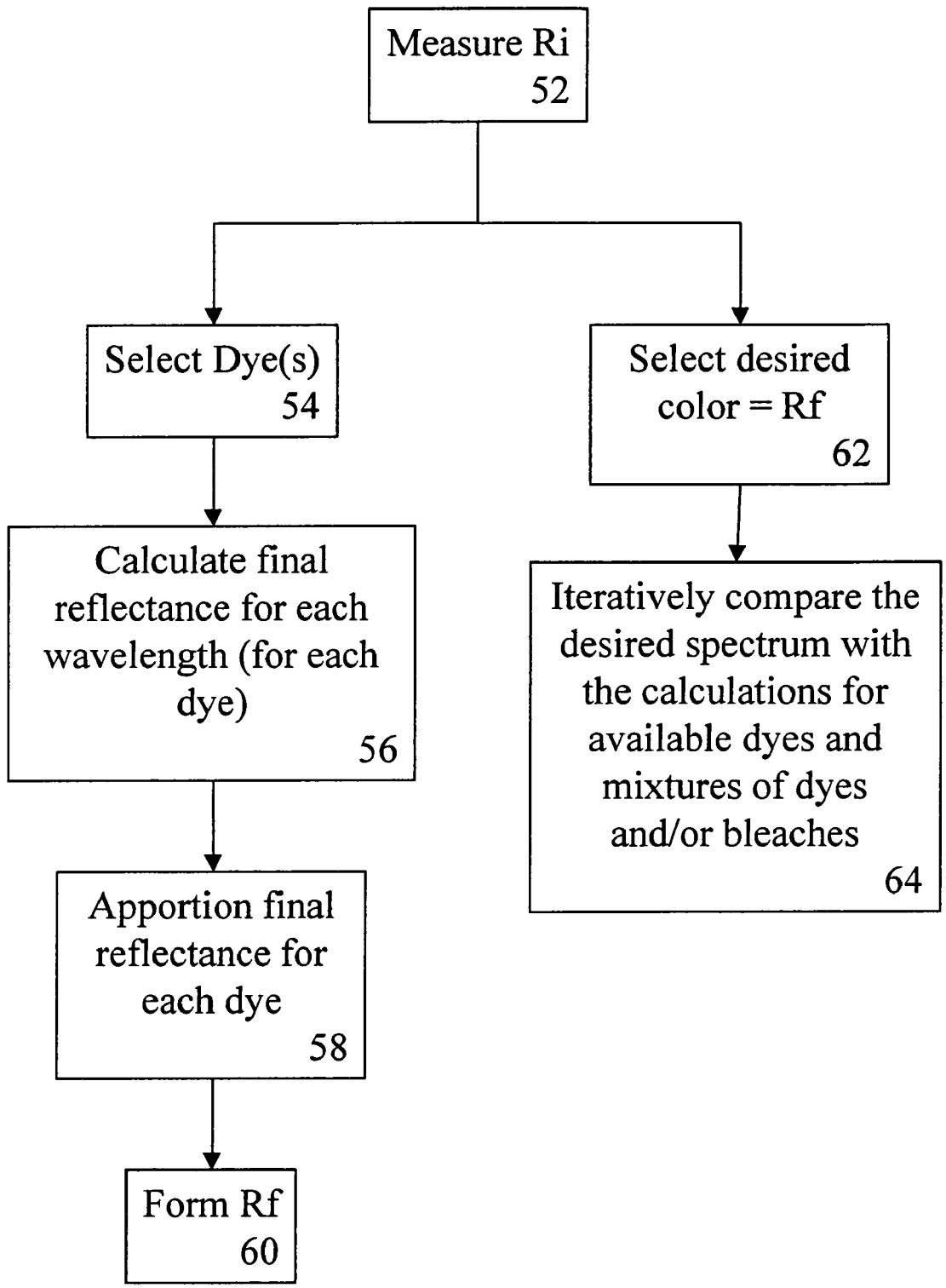
FIG. 8 is a flow chart showing a second approach to calculating a new reflectance spectrum for use with the system of FIG. 1.

FIG. 8 is a flow chart showing the second approach to calculating a new reflectance spectrum for use with the system of FIG. 1. Another way of predicting the final reflectance spectrum of a given hair sample is to view the spectral change caused by a specified hair color treatment at each wavelength of the hair's initial reflectance spectrum separately. As mentioned above, most hair dyes contain bleaching agents. These bleaching agents affect different hair in different ways, depending on their different pigment structure and concentrations. For example, dark hair with a higher concentration of Eumelanin tends to react stronger to bleaching than blond hair with a lower concentration of Eumelanin and a higher concentration of Pheomelanin. Since hair pigments have different light absorbencies at each wavelength, the hair pigment concentrations affect the hair's reflectance at each wavelength differently. For example, a high reflectance value at a certain wavelength can suggest a high concentration of one pigment, while a high reflectance value at another wavelength can be caused by a different pigment. Therefore, the spectral change caused by a hair dye is approximated as a function of the initial reflectance of the hair for each wavelength. Therefore, each hair dye has a plurality of associated spectral change functions, one spectral change function for each wavelength. Once the functions are defined for each wavelength for a specific hair color treatment, the extraction of the final reflectance spectrum is straightforward. So in other words, this second approach involves defining a spectral change function for each wavelength separately and then applying each spectral change function to each wavelength of the initial reflectance measurement in order to arrive at a final reflectance spectrum. Therefore, the spectral change functions vary over the wavelength range of the initial reflectance spectrum.

In more detail the method involves the following basic steps. First, the reflectance difference for each discrete wavelength $\Delta R_{80}$ is calculated using the appropriate spectral change function for that wavelength. Then, the final reflectance value, $R_{f\lambda}$, is calculated by adding the calculated reflectance difference $\Delta R_\lambda$ to the measured initial value of reflectance at that wavelength, $R_{i\lambda}$. at the prediction of the final hair spectrum will be done simply by adding the reflectance difference ($\Delta R_\lambda$) to the measured initial reflectance ($R_{i\lambda}$). This step is represented by the following equation, $$R_{f_\lambda} = R_{i_\lambda} + \Delta R_\lambda. \qquad \text{Equation 3.1}$$

Then all the calculated $R_{f\lambda}$'s for each wavelength are accumulated in order to form a final reflectance spectrum. The term "new optical value" used in the appended claims is defined herein to include a calculated reflectance or absorbency value and a calculated absorbency or reflectance difference of the hair. The term "initial optical value" used in the appended claims is defined herein to include the measured initial value of reflectance at a wavelength, $R_{i\lambda}$ and an initial absorbency value of the hair at a wavelength.

As described with reference to the first approach of FIGS. 2 to 7, the change caused to the reflectance spectrum of the hair by coloring with a mixture of dyes is a combination of the spectral changes of each dye in the mixture. Therefore, prediction of the final color of hair that is colored with a mixture of colors, color 1 and color 2, for a certain wavelength is given by the following equation:

$$R_{f_\lambda} = (R_{f1\lambda})^a \cdot (R_{f2\lambda})^b, \qquad \text{Equation 3.2}$$

where $R_{f\lambda}$ is the final reflectance value at wavelength $\lambda$ after coloring with the color mixture, $R_{f1\lambda}$ and $R_{f2\lambda}$ are the final reflectances at wavelength $\lambda$ as modeled for each hair color treatment separately and a and b are the relative concentrations of the first and second hair color treatment, respectively. Therefore, a+b=1, by definition.

Equation 3.2 is derived as follows. The reflectance after coloring at a certain wavelength can be extracted from Beer's law as, $$R_{f_\lambda} = R_{i_\lambda} \cdot e^{-\alpha_\lambda}, \qquad \text{Equation 3.3}$$

where $e^{-\alpha_\lambda}$ is the spectral change caused by the hair color treatment.

Substituting for $R_{f\lambda}$ in equation 3.3 using equation 3.1 gives, the following equation, $$e^{-\alpha_\lambda} = \frac{R_{i_\lambda} + \Delta R_\lambda}{R_{i_\lambda}}. \qquad \text{Equation 3.4}$$

When coloring with a mixture of two colors the additional spectral change caused by both colors is described by, $$R_{f_\lambda} = R_{i_\lambda} \cdot (e^{-\alpha_{1_\lambda}})^a \cdot (e^{-\alpha_{2_\lambda}})^b, \qquad \text{Equation 3.5}$$

where a and b are the relative concentrations of hair color treatment 1 and hair color treatment 2, respectively.

Substituting $e^{-\alpha_\lambda}$ of equation 3.5 by the right hand side of the equation of equation 3.4 gives, $$R_{f_\lambda} = R_{i_\lambda} \cdot \left(\frac{R_{i_\lambda} + \Delta R_{1_\lambda}}{R_{i_\lambda}}\right)^a \cdot \left(\frac{R_{i_\lambda} + \Delta R_{2_\lambda}}{R_{i_\lambda}}\right)^b, \qquad \text{Equation 3.6}$$

where $\Delta R_{1\lambda}$ and $\Delta R_{2\lambda}$ are the reflectance differences for the first hair color treatment and the second hair color treatment as calculated for each hair color treatment separately (in other words assuming no mixture of colors), respectively.

Since a+b=1, $$R_{f_\lambda} = (R_{i_\lambda} + \Delta R_{1_\lambda})^a \cdot (R_{i_\lambda} + \Delta R_{2_\lambda})^b. \qquad \text{Equation 3.7}$$

Therefore, substituting in equation 3.7 using equation 3.1, gives $$R_f = (R_{f_{1_\lambda}})^a \cdot (R_{f_{2_\lambda}})^b. \qquad \text{Equation 3.8}$$

Equations 3.1 and 3.8 are typically used to calculate a new reflectance spectrum as a direct function of an initial reflectance spectrum and a hypothetical hair treatment. However, it will be appreciated by those ordinarily skilled in the art that equations 3.1 and 3.8 can be used to determine a hypothetical hair treatment as a direct function of an initial reflectance spectrum and a desired final reflectance spectrum. Both these methods are described below.

The first method is for calculating a new reflectance spectrum due to a hypothetical hair treatment as a direct function of an initial reflectance spectrum. First, an initial reflectance spectrum is measured by spectrophotometer 14 (block 52). Second, processor 16 receives the initial reflectance spectrum, having a wavelength range, as an input. Third, at least one hypothetical hair treatment is selected having associated spectral change functions (block 54). Fourth, the final reflectance for each wavelength is calculated. If a mixture of hair color treatments is used, the final reflectance at each wavelength is calculated separately for each hair color treatment (block 56). Next, if a mixture of hair color treatments is used, the calculated reflectance values are apportioned using equation 3.8, for each wavelength (block 58). Finally, a new reflectance spectrum is formed from the calculated final reflectance values (block 60). It is seen that the new spectrum is a substantially non-additive function of the hair treatment and the initial reflectance spectrum.

The second method is for calculating a hair treatment as a direct function of an initial reflectance spectrum and a desired reflectance spectrum. First, an initial reflectance spectrum is measured by spectrophotometer 14 (block 52). Second, processor 16 receives the initial reflectance spectrum, having a wavelength range, as an input. Third, a desired reflectance spectrum is selected (block 62). Finally, for available hair color treatments and mixtures thereof, final reflectance spectra are calculated (block 64) using equations 3.1 and/or 3.8. The final spectra are compared to the desired reflectance spectrum until a close match is found. This process is typically an iterative process in order to reduce processing time. It is seen that the determined hair treatment is a substantially non-additive function of the initial reflectance spectrum and the desired reflectance spectrum.

Figure 9:
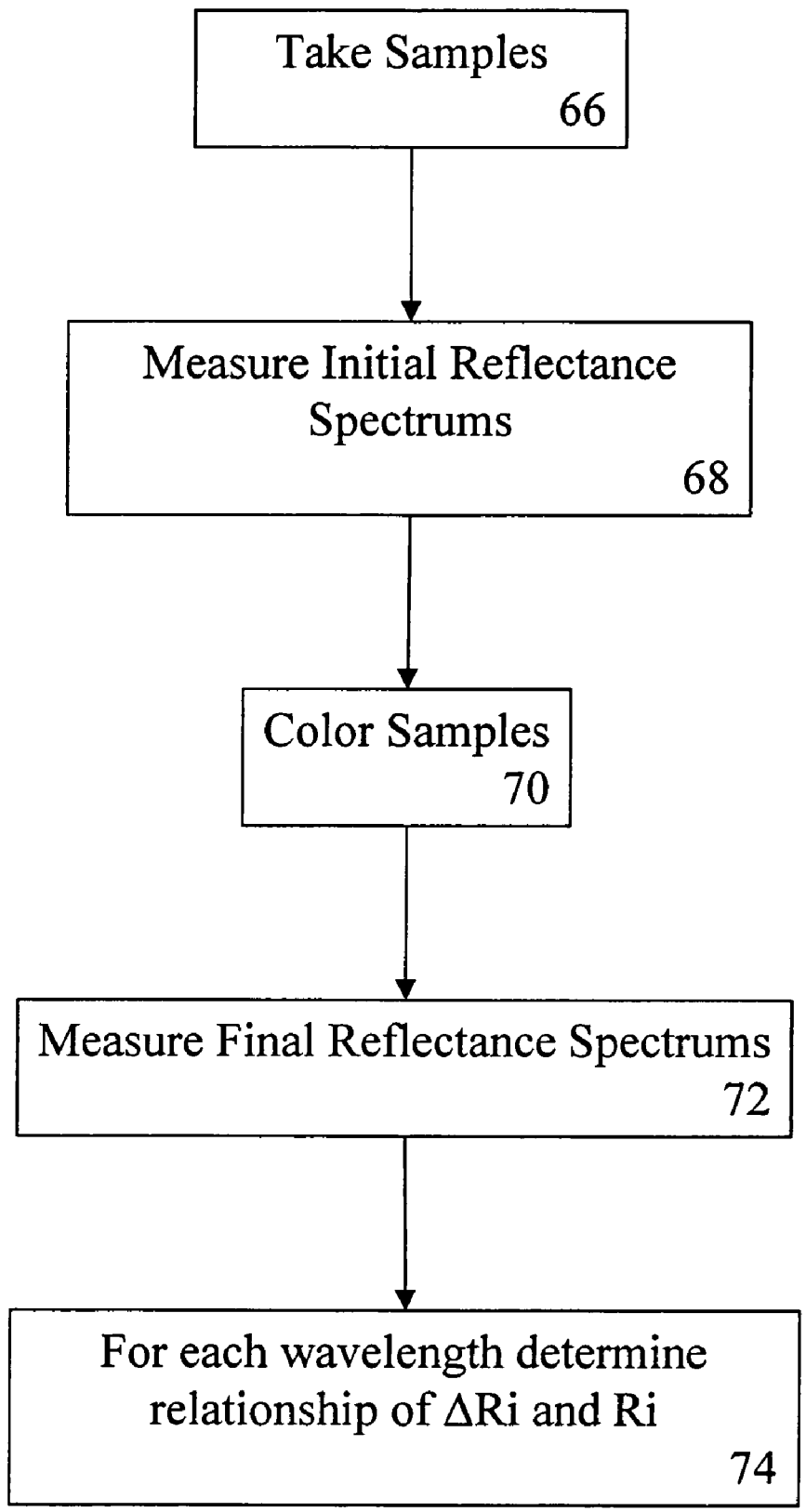
FIG. 9 is a flow chart showing how to create a model for use with the second approach of FIG. 8.
Figure 10:
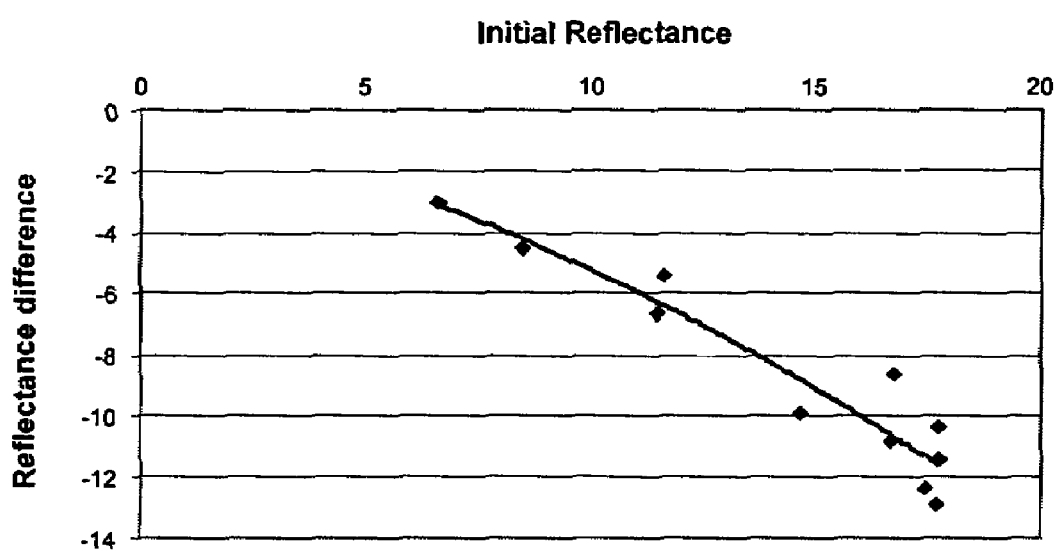
FIG. 10 is a graph of reflectance difference against initial reflectance for one wavelength for a sample of hairs for use with the second approach of FIG. 8.

Reference is now made to FIGS. 9 and 10. FIG. 9 is a flow chart showing how to create a model for use with the second approach of FIG. 8. FIG. 10 is a graph of reflectance difference against initial reflectance for one wavelength for a sample of hairs for use with the second approach of FIG. 8. The steps for constructing this model are as follows. First, several hair samples are taken (block 66). Second, the initial reflectance spectrum of each sample is measured using system 10 (block 68). Third, each sample is colored with the same specific hair color treatment (block 70). Fourth, the final reflectance spectrum of each sample is measured using system 10 (block 72). Finally, for a discrete wavelength of the measured final reflectance spectra, the initial reflectance of the samples at that wavelength, $R_{i\lambda}$, is plotted against the reflectance differences between the final colored hair samples and the initial hair samples at the same wavelength ($\Delta R_\lambda = R_{f_\lambda} - R_{i_\lambda}$) (FIG. 10). A regression function is found that best describes the reflectance difference $\Delta R_\lambda$ as a function of the initial reflectance $R_{i\lambda}$, for example, but not limited to using a least squares method for best fitting a $2^{nd}$ order polynomial function to the reflectance values (block 74). The step of block 74 is repeated for all wavelengths. The above method gives a spectral change function for each wavelength for a specific hair color method. The functions are then used with equations 3.1 and 3.8 as described above with reference to FIG. 8.

Each spectral change function typically has the following quadratic form, $$\Delta R_\lambda = a_\lambda \cdot R_{i_\lambda}^2 + b_\lambda \cdot R_{i_\lambda} + c_\lambda \qquad \text{Equation 3.9,}$$

where $a_\lambda, b_\lambda, c_\lambda$ are constants of the regression function that correlates the initial reflectance with the reflectance difference at a specific wavelength.

Figure 11:
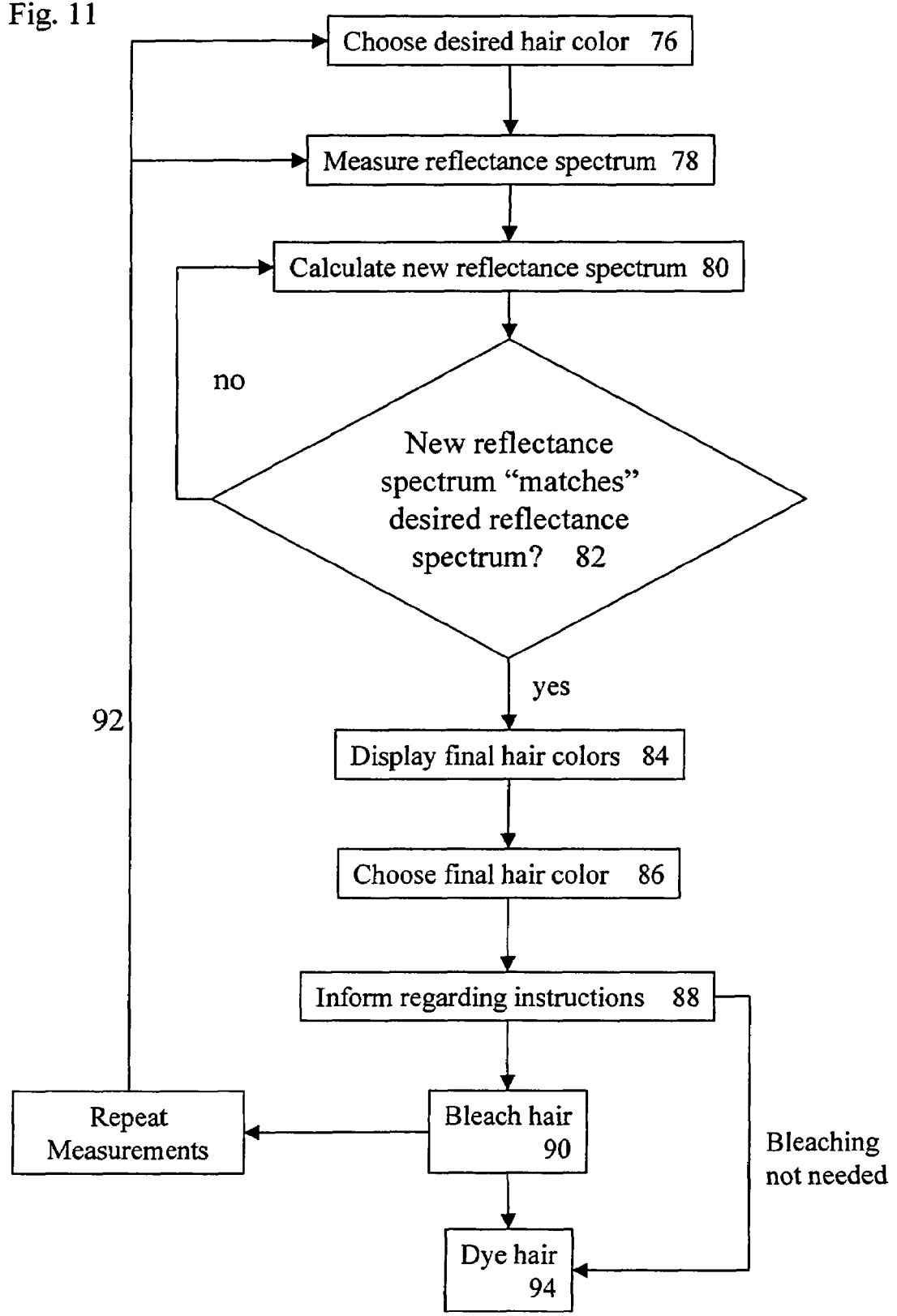
FIG. 11 is a flow chart showing steps in the operation of the system of FIG. 1.

Reference is now made to FIG. 11 is a flow chart showing steps in the operation of system 10 of FIG. 1. First, a customer chooses a desired hair color from a selection of possible hair colors (block 76). The reflectance spectra of the possible hair colors are determined by measurement using system 10. Each reflectance spectrum is then inputted into processor 16. Processor 16 uses the reflectance spectra to recreate the actual color for displaying on a monitor. The displaying of a color on a monitor based upon a reflectance spectrum is known in the art. It will be apparent to those skilled in the art that the desired colors could be printed on a card or be represented as swatches of dyed hair. Therefore, each of the available colors has a known reflectance spectrum. Second, an initial reflectance spectrum of the customer's hair is measured by system 10 (block 78). Third, processor 16 performs calculations based upon hypothetical hair color treatments, including dyeing and/or bleaching as well as mixing two or more dyes, in order to determine a hair color treatment which results in a final reflectance spectrum which is as close as possible to the reflectance spectrum of the desired color. Methods for performing these calculations have been described above with reference to FIGS. 2 and 8. In this step, processor 16 calculates a new reflectance spectrum due to a hypothetical hair color treatment (block 80). This new reflectance spectrum is then compared with the reflectance spectrum of the desired color by subtraction or division of the new reflectance spectrum and the reflectance spectrum of the desired color. Processor 16 then performs many iterative calculations until the difference between the new reflectance spectrum and the desired reflectance spectrum is minimized, given the constraints of the iteration process and the available hair color treatments (block 82). In accordance with an alternate embodiment of the present invention, the desired hair color is represented using a color coordinate presentation, for example, an RGB presentation. The new reflectance spectrum is converted to a color coordinate presentation which is then compared to the color coordinate presentation of the desired hair color. It will be appreciated by those ordinarily skilled in the art that a hair color-treatment can be determined without performing the abovementioned iterative calculations. This alternate method is performed by calculating a desired spectral change function based on the initial reflectance spectrum and the desired final reflectance spectrum. The desired spectral change function is then compared with the spectral change functions of the available hair color treatments and mixtures thereof in order to determine the closest match. Processor 16 then calculates a final reflectance spectrum based upon application of the closest match color treatment. It should be noted that if the desired hair color is a natural hair color, then dyeing using synthetic dyes may not be needed, bleaching may be enough. Likewise, if a customer has light colored hair, additional bleaching may not be necessary to achieve the desired color. Then, after processor 16 has completed the iterative calculations, processor 16 outputs data for displaying a selected number of possible final hair colors on user interface 18 (block 84). This displaying is either, based upon the reflectance spectrum of the final hair color, or the color coordinate presentation of the final hair color. The possible final hair colors generally include the closest match to the desired hair color as well as several other colors, which are a set gap from the desired color. The set gap can be preset by the hairdresser. Then, the customer chooses one of the available final hair colors (block 86). Then, processor 16 outputs data of hair color treatment instructions of the chosen final hair color (which was one of the hypothetical hair color treatments used in the step of block 80) to a device, typically the display of user interface 18, thereby informing the hairdresser of the required bleaching concentrations and bleaching time and/or dye(s) needed to achieve the chosen color (block 88). It will be appreciated by those ordinarily skilled in the art that instead of informing the hairdresser of which dye(s) to use, processor 16 could send data to an automated color (dye and/or bleach) mixing device which dispenses and mixes the dyes and/or bleaches for immediate use by the hairdresser. Next, if bleaching is required, the hairdresser bleaches the hair for the required time (block 90). Then, optionally at this stage, steps of blocks 78 to 88 or block 90, are performed again, before dyeing to achieve more accurate dyeing results (line 92). Then, if dyeing is being performed, the hairdresser dyes the hair using a dye or a combination thereof (block 94). It will be apparent to those skilled in the art that other methods using the technology of the present invention are possible. For example, the above steps may be performed in a different order. Also, the customer could be given a number of hair color choices based on the use of a specific dye with differing bleaching times. Additionally, the customer could be shown on user interface 18 the final hair colors for each of the available dyes. The customer then chooses a hair dye based on the displayed final hair colors without processor 16 performing any comparisons with a desired hair color.

It will be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A system for determining hair color treatment, comprising: a processor configured for:
   (i) receiving as input an initial reflectance spectrum of a sample of hair, said initial reflectance spectrum comprising a plurality of reflectivities at wavelengths over a wavelength range, said reflectivities being accumulated together to form said spectrum;
   (ii) from said initial reflectance spectrum calculating a new reflectance spectrum for said hair due to a hypothetical hair color treatment, said hair color treatment comprising a first hair color treatment associated with a first relative concentration and a first spectral change function and comprising bleaching, and a second color treatment associated with a second relative concentration, and a second spectral change function and comprising dyeing, said calculating comprising using a spectral multiplication function of said initial spectrum, said calculating comprising considering the effect of treatment on reflectivities at individual wavelengths in said initial reflectance spectrum and accumulating said reflectivities to form said new reflectance spectrum, said calculating comprising apportioning of the first and second spectral change functions according to the first and second relative concentrations; and
   (iii) outputting said new reflectance spectrum to a device, thereby to indicate a likely result of applying said hypothetical hair color treatment to said sample of hair.

2. The system of claim 1, further comprising a spectrum analyzer configured for producing said initial spectrum.

3. The system of claim 1, further comprising a display device configured for displaying a color based on said output data.

4. The system of claim 1, further comprising a display device configured for displaying hair color treatment instructions based on said output data.

5. The system of claim 1, further comprising a color mixing device configured for dispensing a hair color treatment based on said output data.

6. The system of claim 1, wherein said processor is further configured for determining a treatment for said hair that gives said hair a desired spectrum.

7. The system of claim 1, wherein said direct function is non-additive.

8. The system of claim 1, wherein said calculating is performed by calculating said new spectrum based on multiplying said input data by a spectral change function over said wavelength range, a value of said spectral change function varying over said wavelength range.

9. The system of claim 8, wherein said spectral change function includes a spectral change component due to a bleaching effect of said hypothetical hair color treatment.

10. The system of claim 9, wherein said spectral change component is dependent upon a reflectance of said hair.

11. The system of claim 9, wherein said spectral change function also includes a spectral change component due to a dyeing effect of said hypothetical hair color treatment.

12. The system of claim 1, wherein said calculating includes:
   (i) for each of a plurality of discrete wavelengths within said wavelength range, calculating a new optical value for said hair, as a function of an initial optical value of said hair, thereby giving a set of new optical values for said hair; and
   (ii) forming said new spectrum from said set of new optical values.

13. The system of claim 12, wherein said function of said initial optical value varies over said wavelength range.

14. A system for determining hair color treatment using a first relative concentration of a first hair color treatment and a second relative concentration of a second hair color treatment, the first hair color treatment having an associated first spectral change function for use in determining a first new spectrum of the hair after application of only the first hair color treatment, said second hair color treatment having an associated second spectral change function for use in determining a second new spectrum of the hair after application of only the second hair color treatment, comprising a processor configured for:
   (i) receiving input data pertaining to an initial reflectance spectrum measured from a sample of hair, said input data representing a measure of reflectance over a finite wavelength range and accumulating said data over said range into a digital version of said spectrum;
   (ii) determining said hair color treatment for said hair as a direct function of said digital version of said spectrum measured from said sample of hair and a desired spectrum of said hair, said direct function comprising spectral multiplication and utilizing said values accumulated over said range, and said desired spectrum likewise being in a format covering said range, said first hair color treatment and said first spectral change function relating to bleaching and said second hair color treatment and said second spectral change function relating to dyeing said calculating comprising apportioning of the first and second spectral change functions according to the first and second relative concentrations; and (iii) outputting data to a device, said output data being based upon said step of determining and being indicative of said determined hair color treatment.

15. The system of claim 14, further comprising a spectrum analyzer configured for producing said data pertaining to said initial measured spectrum.

16. The system of claim 14, further comprising a display device configured for displaying hair color treatment instructions based on said output data.

17. The system of claim 14, further comprising a color mixing device configured for dispensing a hair color treatment based on said output data.

18. The system of claim 14, wherein said function is non-additive.

19. The system of claim 14, wherein said determining includes: calculating a spectral change function by dividing said desired spectrum by said initial directly measured spectrum over said wavelength range; and determining said treatment from said spectral change function.

20. The system of claim 19, wherein said spectral change function includes a spectral change component due to a bleaching effect of said hypothetical hair color treatment.

21. The system of claim 20, wherein said spectral change component is dependent upon a reflectance of said hair.

22. The system of claim 20, wherein said spectral change function also includes a spectral change component due to a dyeing effect of said hypothetical hair color treatment.

23. The system of claim 14, wherein said determining includes for each of a plurality of discrete wavelengths within said wavelength range, calculating a new optical value for said hair for one of said discrete wavelengths as a function of an initial optical value of said hair at said one discrete wavelength, thereby giving a set of new optical values for said hair.

24. The system of claim 23, wherein said function of said initial optical value varies over said wavelength range.

25. A system for determining treatment of hair using a first relative concentration of a first hair color treatment and a second relative concentration of a second hair color treatment, the first hair color treatment having an associated first spectral change function for use in determining a first new spectrum of the hair after application of only the first hair color treatment, said second hair color treatment having an associated second spectral change function for use in determining a second new spectrum of the hair after application of only the second hair color treatment, the system comprising a processor configured for:

(i) receiving input data pertaining to an initial spectrum measured from the hair, said input data representing a measure of reflectance over a finite wavelength range, wherein said input data comprises an accumulation of reflectance intensity values over said wavelength range to form said initial spectrum;

(ii) using said input data pertaining to said initial spectrum as said accumulation of spectral values over said range, measured from the hair, calculating a new spectrum of the hair due to a hypothetical hair color treatment of applying the first relative concentration of the first hair color treatment and the second relative concentration of a the second hair color treatment to the hair, said new spectrum likewise being in said format comprising an accumulation of spectral values over said wavelength range, said calculating said calculating comprising using a spectral multiplication function of said initial spectrum, and being based upon:

apportioning the first spectral change function and the second spectral change function by the first relative concentration and the second relative concentration, respectively, wherein the first spectral change function is a function defining a change in a hair sample spectrum due to bleaching, and the second spectral change function is a function defining a change in a hair sample spectrum due to dyeing; and (iii) outputting data to a device, said data being based on said step of calculating, said data being indicative of said first and second relative concentrations for achieving said new spectrum.

26. The system of claim 25, wherein said calculating is based on at least one of:

(i) raising the first spectral change function to a power of the first relative concentration and raising the second spectral change function to a power of the second relative concentration; and (ii) raising the first new spectrum to a power of the first relative concentration and raising the second new spectrum to a power of the second relative concentration.

27. The system of claim 25, further comprising a spectrum analyzer configured for producing said data pertaining to said initial measured spectrum.

28. The system of claim 25, further comprising a display device configured for displaying a color based on said output data.

29. The system of claim 25, further comprising a display device configured for displaying hair color treatment instructions based on said output data.

30. The system of claim 25, further comprising a color mixing device configured for dispensing a hair color treatment based on said output data.

31. A method for determining a hypothetical hair color treatment, the hair color treatment using a first relative concentration of a first hair color treatment and a second relative concentration of a second hair color treatment, the first hair color treatment having an associated first spectral change function for use in determining a first new spectrum of the hair after application of only the first hair color treatment, said second hair color treatment having an associated second spectral change function for use in determining a second new spectrum of the hair after application of only the second hair color treatment, comprising the steps of:

(i) receiving input data pertaining to an initial reflectance spectrum measured from a sample of hair, said input data representing a measure of reflectance values accumulated over a finite wavelength range as a digital version of said initial spectrum ; and (ii) calculating a new spectrum of said hair due to said hypothetical hair color treatment as a direct function of said data pertaining to said initial spectrum measured from said hair, said direct function comprising spectral multiplication and utilizing said accumulated spectral values as a function of wavelength, such that said new spectrum likewise comprises spectral values accumulated over a wavelength range, said first hair color treatment method and said first spectral change function being associated with bleaching and said second hair color treatment method and said second spectral change function being associated with dyeing, said calculating comprising apportioning of the first and second spectral change functions according to the first and second relative concentrations; and (iii) outputting data indicative of said hypothetical hair color treatment to a device, said output data being based upon said step of calculating.

32. The method of claim 31, further comprising the step of displaying a color based on said new spectrum.

33. The method of claim 31, further comprising the step of displaying hair color treatment instructions based on said new spectrum.

34. The method of claim 31, further comprising the step of dispensing a hair color treatment based on said new spectrum.

35. The method of claim 31, further comprising the step of determining a treatment for said hair that gives said hair a desired spectrum.

36. The method of claim 31, wherein said direct function is non-additive.

37. The method of claim 31, wherein said calculating is performed by calculating said new spectrum, based on multiplying said input data by a spectral change function over said wavelength range, a value of said spectral change function varying over said wavelength range.

38. The method of claim 37, wherein said spectral change function includes a spectral change component due to a bleaching effect of said hypothetical hair color treatment.

39. The method of claim 38, wherein said spectral change component is dependent upon a reflectance of said hair.

40. The method of claim 38, wherein said spectral change function also includes a spectral change component due to a dyeing effect of said hypothetical hair color treatment.

41. The method of claim 31, wherein said calculating includes:

(i) for each of a plurality of discrete wavelengths within said wavelength range, calculating a new optical value for said hair, as a function of an initial optical value of said hair, thereby giving a set of new optical values for said hair; and (ii) forming said new spectrum from said set of new optical values.

42. The method of claim 41, wherein said function of said initial optical value varies over said wavelength range.

43. A computer software product, comprising a computer readable medium in which computer instructions are stored, which instructions when read by a computer, causes the computer to determine a hair color treatment, the instructions including the steps of claim 31.

44. A method for determining hair color treatment, the treatment of hair using a first relative concentration of a first hair color treatment and a second relative concentration of a second hair color treatment, the first hair color treatment having an associated first spectral change function for use in determining a first new spectrum of the hair after application of only the first hair color treatment, said second hair color treatment having an associated second spectral change function for use in determining a second new spectrum of the hair after application of only the second hair color treatment, comprising the steps of:

(i) receiving input data pertaining to an initial reflectance spectrum measured from a sample of hair, said input data representing a measure of reflectance over a finite wavelength range, wherein said input data comprises accumulated intensity values over said wavelength range, said values being accumulated to form a digital version of said initial reflectance spectrum;

(ii) determining a hair color treatment for said hair as a spectral multiplication function of said data pertaining to said initial spectrum measured from said sample of hair and a desired spectrum of said hair, said direct function utilizing said format comprising said intensity values, and said desired spectrum being expressed using said intensity values, said hair color treatment being determined in terms of said first and second hair color treatments and associated spectral change functions, said first hair color treatment and said first spectral change function relating to bleaching, and said second hair color treatment and said second spectral change function relating to dyeing, said calculating comprising apportioning of the first and second spectral change functions according to the first and second relative concentrations; and (iii) outputting data indicative of said determined hair color treatment to a device, said output data being based upon said step of determining.

45. The method of claim 44, further comprising the step of displaying hair color treatment instructions based on said determining.

46. The method of claim 44, further comprising the step of dispensing a hair color treatment based on said determining.

47. The method of claim 44, wherein said function is non-additive.

48. The method of claim 44, wherein said determining includes: calculating a spectral change function by dividing said desired spectrum by said input data over said wavelength range; and determining said treatment from said spectral change function.

49. The method of claim 48, wherein said spectral change function includes a spectral change component due to a bleaching effect of said hypothetical hair color treatment.

50. The method of claim 49, wherein said spectral change component is dependent upon a reflectance of said hair.

51. The method of claim 49, wherein said spectral change function also includes a spectral change component due to a dyeing effect of said hypothetical hair color treatment.

52. The method of claim 44, wherein said determining includes for each of a plurality of discrete wavelengths within said wavelength range, calculating a new optical value for said hair, as a function of an initial optical value of said hair, thereby giving a set of new optical values for said hair.

53. The method of claim 52, wherein said function of said initial optical value varies over said wavelength range.

54. A computer software product, comprising a computer readable medium in which computer instructions are stored, which instructions when read by a computer, causes the computer to determine a hair color treatment, the instructions including the steps of claim 44.

55. A method for determining a hair color treatment using a first relative concentration of a first hair color treatment and a second relative concentration of a second hair color treatment, the first hair color treatment having an associated first spectral change function for use in determining a first new spectrum of the hair after application of only the first hair color treatment, the second hair color treatment having an associated second spectral change function for use in determining a second new spectrum of the hair after application of only the second hair color treatment, the method including the steps of:

(i) receiving input data pertaining to an initial spectrum measured from a sample of the hair, said input data representing a measure of reflectance over a finite wavelength range, wherein said input data has a format comprising intensity values accumulated as a spectrum over a wavelength range; and (ii) using said input data, calculating a new spectrum of the hair due to a hypothetical hair color treatment of applying the first relative concentration of the first hair color treatment and the second relative concentration of the second hair color treatment to the hair, said calculating comprising spectral multiplication over said wavelength range, such that said new spectrum is likewise an accumulation over a wavelength range, said calculating further being based upon apportioning the first spectral change function and the second spectral change function by the first relative concentration and the second relative concentration, respectively;

(III) outputting data indicative of said first and second relative concentrations to a device, said data being based upon said step of calculating, the first concentration being a bleaching concentration and the second concentration being a dyeing concentration.

56. The method of claim 55, wherein said calculating is based on at least one of:

(i) raising the first spectral change function to a power of the first relative concentration and raising the second spectral change function to a power of the second relative concentration; and (ii) raising the first new spectrum to a power of the first relative concentration and raising the second new spectrum to a power of the second relative concentration.

57. A computer software product, comprising a computer readable medium in which computer instructions are stored, which instructions when read by a computer, causes the computer to determine a hair color treatment using a first relative concentration of a first hair color treatment and a second relative concentration of a second hair color treatment, the first hair color treatment having an associated first spectral change function for use in determining a first new spectrum of the hair after application of only the first hair color treatment, said second hair color treatment having an associated second spectral change function for use in determining a second new spectrum of the hair after application of only the second hair color treatment, the instructions including the steps of claim 55.

* * * * *